United States Patent
Zhang et al.

(10) Patent No.: US 12,398,369 B2
(45) Date of Patent: Aug. 26, 2025

(54) PURIFIED DOUBLE NEGATIVE T CELL AND PREPARATION AND USE THEREOF

(71) Applicant: BEIJING IMMUTECH LLC, Beijing (CN)

(72) Inventors: Dong Zhang, Beijing (CN); Yanbing Zhu, Beijing (CN); Lu Yang, Beijing (CN); Dan Tian, Beijing (CN); Song Wang, Beijing (CN); Guangyong Sun, Beijing (CN)

(73) Assignee: BEIJING IMMUTECH LLC, Beijing (CN)

( * ) Notice: Subject to any disclaimer, the term of this patent is extended or adjusted under 35 U.S.C. 154(b) by 857 days.

(21) Appl. No.: 17/616,755

(22) PCT Filed: Apr. 28, 2020

(86) PCT No.: PCT/CN2020/087606
§ 371 (c)(1),
(2) Date: Dec. 6, 2021

(87) PCT Pub. No.: WO2020/244345
PCT Pub. Date: Dec. 10, 2020

(65) Prior Publication Data
US 2022/0331359 A1    Oct. 20, 2022

(30) Foreign Application Priority Data
Jun. 4, 2019   (CN) .................. 201910483156.2

(51) Int. Cl.
| A61K 35/17 | (2025.01) |
| A61K 40/11 | (2025.01) |
| A61K 40/22 | (2025.01) |
| A61K 40/41 | (2025.01) |
| A61P 11/06 | (2006.01) |
| A61P 37/02 | (2006.01) |
| C12N 5/00 | (2006.01) |
| C12N 5/0783 | (2010.01) |

(52) U.S. Cl.
CPC ............ C12N 5/0081 (2013.01); A61K 40/11 (2025.01); A61K 40/22 (2025.01); A61K 40/416 (2025.01); A61P 11/06 (2018.01); A61P 37/02 (2018.01); C12N 5/0636 (2013.01); *A61K 2239/38* (2023.05)

(58) Field of Classification Search
CPC . A61K 39/4611; C12N 5/0636; C12N 5/0081
See application file for complete search history.

(56) References Cited

U.S. PATENT DOCUMENTS

2018/0312808 A1* 11/2018 Hayday ............... A61K 39/4644

FOREIGN PATENT DOCUMENTS

| CN | 105483083 A | 4/2016 |
| CN | 105483083 | * 10/2016 |
| WO | 2007056854 A1 | 5/2007 |

OTHER PUBLICATIONS

Kuriya et al., Diabetologia, 2013, 56:1773-1780.*
Duncan et al., PLoS One, 2010, 5(7), e11427: 1-13.*
Tian et al., Nature Communications, 2019, 10:246, pp. 1-13.*
Qiao, Guhin et al.; "A77 1726, the active metabolite of leflunomide, attenuates lupus nephritis by promoting the development of regulatory T cells and inhibiting IL-17-producing double negative T cells"; Clirncal Immunology, Jan. 28, 2015, vol. 157, pp. 166-174.
Zhang, D. et al.; "Adoptive cell therapy using antigen-specific CD4 CD8 T regulatory cells to prevent autoimmune diabetes and promote islet allograft survival in NOD mice"; Diabetologia, May 19, 2011, vol. 54(8), 2082-2092, pp. 1-12.
International Search Report and Written Opinion; PCT Application No. PCT/CN2020/087606; mailed Jul. 29, 2020.
English translation of International Search Report; PCT Application No. PCT/CN2020/087606; mailed Jul. 29, 2020.
English abstract of CN105483083; retrieved from www.espacenet.com on Dec. 3, 2021.
Zho, Yue et al., "DNT: Preposition: Research Progress on DNT Cells in Immunotherapy"; International Journal of Surgery, vol. 40, No. 8, pp. 557-560; Aug. 15, 2013.
Crispin, JC et al., "Expanded Double Negative T Cells in Patients with Systemic Lupus Erythematosus Produce IL-17 and Infiltrate the Kidneys"; Journal of Immunology, vol. 181, No. 12, pp. 8761-8766; Dec. 15, 2008.

* cited by examiner

*Primary Examiner* — Hong Sang
(74) *Attorney, Agent, or Firm* — NKL Law; Bin Lu; Allen Xue

(57) ABSTRACT

Provided is a DNT cell population with IL-17 secretory cells removed and a preparation method therefor and the use thereof. The DNT cell population has the effects of inhibiting T cell proliferation and inducing apoptosis, can inhibit the inflammation of adipose tissue, improve insulin resistance, alleviate diabetes, and relieve steatohepatitis, and can also be used for preventing and treating antigen-specific allergic asthma.

13 Claims, 9 Drawing Sheets

PURIFIED DOUBLE NEGATIVE T CELL AND PREPARATION AND USE THEREOF

CROSS REFERENCE TO RELATED APPLICATIONS

The present application is the U.S. National Phase under 35 U.S.C. § 371 of International Application No. PCT/CN2020/087606, filed Apr. 28, 2020, which claims the priority of the Chinese patent application filed with the Chinese Patent Office on Jun. 4, 2019, with the application number CN201910483156.2 and the invention title of "Purified double negative t cell and preparation and use thereof", the entire contents of each of which are herein incorporated by reference.

TECHNICAL FIELD

The present invention relates to the field of biomedicine, and in particular to a purified double negative T cell and preparation and use thereof.

BACKGROUND

Double negative T cells (DNT cells) are a kind of T lymphocyte with unique phenotype TCRαβ+, and do not express cell surface markers which are characteristically expressed by CD4 cells, CD8 cells, NK cells etc. Although the DNT cells account for only 1%-3% of the total T lymphocytes in peripheral blood and lymphoid organs of human and mouse, it is proved by more and more studies that such rare T cell population plays a key and diversified role of regulation in the immune system.

Most studies show that DNT cells play a crucial role in maintaining antigen-specific immune homeostasis. DNT cells can highly express perforin, granzyme B and FasL, and show strong immunosuppressive activity on CD4 and CD8 T cells, B cells, dendritic cells and NK cells so that DNT cells can down regulate the excessive immune response of the organism, so as to inhibit transplantation rejection, avoid the occurrence of graft-versus-host disease and effectively control the occurrence and development of autoimmune diseases. DNT cells is also useful in tumor cell killing therapy since they highly express cell killing related proteins such as granzyme and perforin. Based on these findings, there are many studies focusing on the in vitro amplification of DNT cells for organ transplantation rejection, graft-versus-host disease, autoimmune diseases, and even prevention and treatment of cancer. In these studies, mononuclear cells are mainly separated from human peripheral blood or mouse spleen cells, and expanded after the CD4, CD8 and CD56 (in human)/NK1.1 (in mouse) cells are removed. After further removing CD4, CD8 and CD56 (in human)/NK1.1 (in mouse) cells from the expanded cells, the remaining cells are used for adoptive transfer treatment.

Although it is found in studies that DNT cells have the ability of antigen-specific immunosuppression, such as targeted prevention and treatment of transplantation rejection and autoimmune diabetes, it is unknown how DNT cells retain specific recognition of MHC-II antigen, because DNT cells lack CD4 molecule, which is a key molecule to identify MHC-II molecules. Therefore, a further research of DNT cells and their application is urgently needed in this field.

SUMMARY OF INVENTION

The purpose of the invention is to provide a purified double negative T cell and preparation and use thereof.

In the first aspect of the present invention, it provides a cell preparation, which comprises a DNT cell population, in which cells secreting and expressing no IL-17 are more than 95%, preferably more than 98%, more preferably more than 99%, and most preferably more than 99.9% of the total cell number.

In another preferred embodiment, in the DNT cell population, more than 95% cells of the total cells comprise surface antigen CD3+ and TCR.

In another preferred embodiment, CD3 is normally expressed or low expressed and TCRαβ is normally expressed or low expressed in cells in the DNT cell population.

In another preferred embodiment, in the DNT cell population, over 95% cells of the total cell number do not express the surface marker selected from the group consisting of CD4, CD8, NK1.1 (in mouse)/CD56 (in human), and a combination thereof.

In another preferred embodiment, in the DNT cell population, over 95% cells of the total cells (or total cell number) express a gene selected from the group consisting of CCR5, CXCR3, B220, FasL, NKG2D, perforin, granzyme B, and a combination thereof.

In another preferred embodiment, in the DNT cell population, cells with high expression of LAG3 gene account for more than 50%, preferably more than 70%, and more preferably more than 90% of the total cell number.

In another preferred embodiment, the high expression means that the ratio of LAG3 gene expression level G1 of the cell to LAG3 gene expression level G0 of the normal CD4 T cell, i.e. G1/G0, is ≥1.2, preferably ≥1.5, and more preferably ≥2.

In another preferred embodiment, the low expression means that the ratio of a specific gene expression level R1 of the cell to an expression level R0 of the same gene of the normal CD4 T cell, i.e. R1/R0, is ≤1, preferably ≤0.8, and more preferably ≤0.5.

In another preferred embodiment, the cells in the DNT cell population have antigen specificity.

In another preferred embodiment, the cell preparation consists of the DNT cell population and a pharmaceutically acceptable carrier.

In the second aspect of the present invention, it provides a method for preparing the cell preparation according to the first aspect of the present invention, which comprises steps of:
(a) providing a mononuclear cell population (or PBMCs) and sorting the cell population, thereby obtaining a first cell subpopulation dominated by DNT cells;
(b) removing IL-17 producing DNT cells from the first cell subpopulation and culturing and amplifying (or amplification culturing) the remained first cell subpopulation, thereby obtaining a second cell subpopulation; or
amplification culturing the first cell subpopulation and then removing IL-17 producing DNT cells, thereby obtaining a second cell subpopulation;
(c) optionally, further sorting DNT cells in the second cell subpopulation, thereby obtaining a third cell subpopulation; and
(d) mixing the second or third cell subpopulation with an appropriate carrier, thereby obtaining the cell preparation according to the first aspect of the present invention.

In another preferred embodiment, in step (a), the B cells, CD4 T cells and CD8 T cells, γδ T cells, type 1 NKT cells and type 2 NKT cells are removed from the mononuclear cell population, thereby obtaining the first cell subpopulation dominated by DNT cells.

In another preferred embodiment, in step (a), the PBMCs are negative sorted after being labeled with an antibody against CD19, CD4, CD8, TCR-γδ, NK1.1 (for mouse)/CD56 (for human), aGalcer-CD1d or LPC-CD1d tetramer (or TCRVα24-Jα18 antibody), thereby obtaining the first cell subpopulation dominated by DNT cells.

In another preferred embodiment, the negative sorting is selected from the group consisting of magnetic bead sorting, fluorescence activated cell sorting and density gradient centrifugation.

In another preferred embodiment, in step (b), the IL-17 producing DNT cells are removed before culturing by using one or more antibodies targeting an expression protein selected from the group A comprising S100a6, Tmem176b, CXCR6, Ramp1, Tmem176a, Lgals1, Lgals3, ACTN2, ICOS, CCR2, CD82, CD127(IL7r), Ltb4r1, Hk2, TNFRSF25, Ly6a, BLK, Lsp1, Ly6e, Itgb7, Itm2b, S100a10, Ly6g5b, Thy1, CD40lg, Ramp3, Gm2a and a combination thereof;

and preferably, the group A comprises S100a6, CXCR6, ICOS, CCR2, CD82, CD127, Ltb4r and a combination thereof.

In another preferred embodiment, in step (b), the IL-17 producing DNT cells are removed from culture system after culturing by using one or more antibodies targeting an expression protein selected from the group B comprising IL-17a, Lgals1, Ly6a, CXCR6, S100a6, Lgals3, Lta, IL-4, IL-3, ICOS, S100a10, Ramp1, Tmem176b, Tnfrsf4, AA467197, Itm2b, Thy1, Igtp, Arl6ip1, Serpine2, Ltb, Tnfrsf25, Furin, Tmem176a, Ifi27l2a, Gbp2, Emp3, Ltb4r1, Tspo, Cst3, Vim, CD200 and a combination thereof;

and preferably, the group B comprises Lgals1, Ly6a, CXCR6, S100a6, Lgals3, Lta, ICOS, S100a10, Tnfrsf4 and a combination thereof.

In another preferred embodiment, in step (b), the amplification culture is performed in the presence of a T cell stimulator selected from the group consisting of:

concanavalin A (Con A), phytohemagglutinin (PHA), PMA, ionomycin, IPP, Pamidronate, Zoledronate, CD2 antibody or magnetic bead labeled with CD2 antibody, CD3 antibody or magnetic bead labeled with CD3 antibody, CD28 antibody or magnetic bead labeled with CD28 antibody, and a combination thereof.

In another preferred embodiment, in step (b), a cytokine selected from the group consisting of IL-2, IL-15, and a combination thereof is added during amplification culture.

In another preferred embodiment, in step (b), the amplification culturing is performed in the presence of an antigen-present cell and/or an antigen peptide.

In another preferred embodiment, the antigen-present cell comprises macrophage, dendritic cell, and/or B cell.

In another preferred embodiment, the antigen peptide comprises an antigen peptide related to allergen, such as dust mite antigen peptide, pollen antigen peptide, and tree powder antigen peptide.

In another preferred embodiment, the antigen peptide comprises antigen peptide related to autoimmune diseases.

In another preferred embodiment, the antigen peptide is selected from the group consisting of:
  (i) allergen polypeptide related to asthma;
  (ii) GAD65 antigen peptide and insulin antigen peptide related to type 1 diabetes;
  (iii) ENA polypeptide, nucleoprotein antigen polypeptide and cytoplasm protein antigen polypeptide related to rheumatic autoimmune diseases; and
  (iv) mitochondria antigen peptide and liver antigen peptide related to autoimmune liver diseases.

In another preferred embodiment, in step (b), the duration of amplification culture ranges from 14 to 21 days.

In another preferred embodiment, in step (b), the amplification culture is performed in vitro.

In another preferred embodiment, in step (c), the CD4 and CD8 T cells and NK cells are removed from the second cell subpopulation, thereby obtaining the third cell subpopulation.

In another preferred embodiment, in step (c), the DNT cells in the second cell subpopulation are negative sorted after being labeled using an antibody against CD4, CD8, NK1.1 (for mouse)/CD56 (for human), thereby obtaining the third cell subpopulation.

In another preferred embodiment, in step (b), the carrier is isotonic solution.

In another preferred embodiment, in step (d), the carrier is selected from the group consisting of:

PBS, HESS, normal saline, Lactated Ringer's Solution, plasma, isotonic solution containing serum albumin, cell preserve fluid without serum, and a combination thereof.

In another preferred embodiment, the mononuclear cells (PBMCs) are obtained from mammals, more preferably from human.

In another preferred embodiment, in step (a), the mononuclear cell population comprising mononuclear cells derived from peripheral blood or spleen.

In the third aspect of the present invention, it provides use of the cell preparation according to the first aspect of the present invention in preparing a pharmaceutical composition for treating a disease selected from the group consisting of tumor, infection disease, transplantation rejection, graft-versus-host disease, allergic asthma, autoimmune disease, metabolic syndrome, stroke, and a combination thereof.

In another preferred embodiment, the metabolic syndrome comprises: obesity, insulin resistance, type 2 diabetes, steatohepatitis, coronal atherosclerosis heart disease, and a combination thereof.

In another preferred embodiment, the autoimmune diseases comprises: type 1 diabetes, lupus erythematosus, rheumatoid arthritis, Sjogren's Syndrome, psoriasis, multiple sclerosis, autoimmune hepatitis, primary biliary cirrhosis, primary sclerosing cholangitis, Hashimoto's thyroiditis, autoimmune kidney disease and a combination thereof.

In the fourth aspect of the present invention, it provides a pharmaceutical composition, which comprises the cell preparation prepared by the method according to the second aspect of the present invention, and a pharmaceutically acceptable carrier, diluent or excipient.

In another preferred embodiment, the pharmaceutical composition is a liquid preparation.

In the fourth aspect of the present invention, it provides a method for inhibiting the proliferation of T cells and/or inducing apoptosis of T cells, which comprises a step of:

administering the composition according to the first aspect of the present invention, or a medicament containing the composition as an active ingredient to a subject in need of.

In another preferred embodiment, the method further inhibits inflammation of adipose tissue and improves insulin resistance.

In another preferred embodiment, the method further prevent and treat asthma based on antigen specificity.

It is to be understood that the various technical features of the present invention mentioned above and the various technical features specifically described hereinafter (as in the Examples) may be combined with each other within the scope of the present invention to constitute a new or preferred technical solution, which will not be redundantly repeated one by one herein, due to space limitations.

DESCRIPTION OF DRAWINGS

FIG. 9A shows the experimental process. Specifically, after high-fat diet for 8 weeks, the mice were administered with a single infusion of DNT cells followed by high-fat diet for another 8 weeks. FIG. 9B shows that after DNT cells infusion, the weight increase of mice was significantly less than the simple high-fat diet group. FIG. 9C shows that liver fat follicle degeneration and inflammatory cell accumulation of mice were significantly improved in the DNT cells treated group. FIG. 9D shows that fasting blood sugar of mice in the DNT cells treated group was significantly decreased than that in the simple high-fat diet group.

EMBODIMENTS

Figure 1:
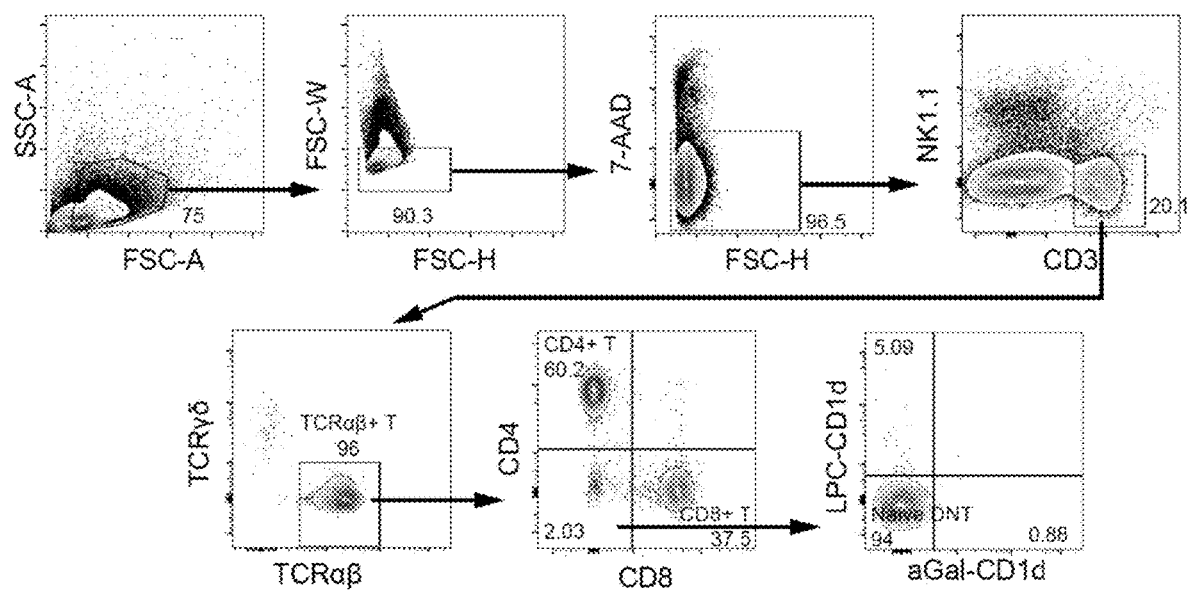
FIG. 1 shows the graphs of the purification and flow cytometry detection of double negative T cell (in the circumstance that in the conventional method, only TCR-γδ, CD4, CD8 and NK1.1 positive cells are removed, there are still nearly 6% of NKT cells in the remaining TCRαβ$^+$CD4$^-$CD8$^-$NK1.1$^-$ DNT cells).

After extensive and intensive studies, the inventors have unexpectedly discovered that removing the IL-17 producing DNT cells from the DNT cell population can significantly inhibit T cell proliferation, induce apoptosis, inhibit the inflammation of adipose tissue and improve insulin resistance, and also have the effect of preventing and treating asthma based on antigen specificity.

DNT Cells

DNT cells, namely double negative T cells, are a kind of TCRαβ+T lymphocytes with unique phenotype, do not express cell surface markers which are characteristically expressed by CD4 cells, CD8 cells, NK cells, and play a key and diversified role of regulation in the immune system.

The present invention provides a DNT cell population from which IL-17 producing cells are removed, which has significant effects of inhibiting T cell proliferation and inducing apoptosis, and can inhibit the inflammation of adipose tissue and improve insulin resistance.

As used herein, the term naïve DNT cell means natural DNT cell.

Purification and Amplification of DNT Cells

In the present application, the purification of DNT cells can be performed before or after the culture amplification. Preferably, the IL-17 producing DNT cells are pre-removed before the culture amplification of DNT cells, because the amount of antibody in the former method is significantly less than that in the latter method. Specifically, the two purification methods are indicated below.

1. Purification before amplification, i.e., pre-removal of the IL-17 producing naïve DNT cell subpopulation before amplification of DNT cells.

PBMCs are obtained from mice or human spleen or peripheral blood under sterile condition. Mononuclear cell suspension is obtained via gradient centrifugal method. The mononuclear cells are labeled with antibodies against CD19, CD4, CD8, TCR-γδ, NK1.1 (for mouse)/CD56 (for human), aGalcer-CD1d and LPC-CD1d tetramer (or TCRVα24-Jα18 antibody) (in order to remove B cells, CD4 and CD8 T cells, γδ T cells, type 1 NKT cells and type 2 NKT cells respectively) and then negative sorted (via sorting methods such as magnetic bead sorting, fluorescence activated cell sorting, density gradient centrifugation, etc.), thereby obtaining a cell subpopulation dominated by DNT cells. At the same time, the IL-17 producing DNT cell subpopulation is removed by using an antibody targeting S100a6, CXCR6, ICOS, CCR2, CD82, CD127 or Ltb4r, or a combination of these antibodies. Then DNT cells are stimulated for amplification by using any agent that can stimulate the amplification of DNT cells, e.g. concanavalin A (Con A), phytohemagglutinin (PHA), PMA, ionomycin, IPP, Pamidronate, Zoledronate and anti-CD2 antibody, anti-CD3 antibody and anti-CD28 antibody or magnetic bead labeled with these antibodies, or a combination thereof. As for a combination, the agents can be mixed in any proportion. In order to increase the proliferation rate of DNT cells, various cytokines such as IL-2 and/or IL-15 or the combination thereof can be added. Culture time is 14-21 days. During the culture, medium and plate are exchanged depending on the condition of medium and cell density. After culture, negative sorting is performed by using magnetic beads labeled with antibody against CD4, CD8 and NK1.1 (for mouse)/CD56 (for human), so as to remove the possible CD4, CD8 and NK cells from the culture and obtain cultured DNT cells for subsequent therapy. The phenotype of cultured and amplified DNT cells is CD3+TCRαβ±CD4−CD8−NK1.1− (for mouse)/CD56− (for human) CD19−TCRγδ±.

2. Purification after amplification, i.e., removing the IL-17 producing naïve DNT cells after amplification of DNT cell subpopulation. PBMCs are obtained from mice or human spleen or peripheral blood under sterile condition. Mononuclear cell suspension is obtained via gradient centrifugal method. The mononuclear cells were labeled with antibodies against CD19, CD4, CD8, TCR-γδ, NK1.1 (for mouse)/CD56 (for human), aGalcer-CD1d and LPC-CD1d tetramer (or TCRVα24-Jα18 antibody) and negative sorted by using magnetic beads to obtain DNT cells. Then DNT cells are stimulated for amplification by using any agent that can stimulate the amplification of DNT cells, e.g. concanavalin A (Con A), phytohemagglutinin (PHA), PMA, ionomycin, IPP, Pamidronate, Zoledronate and anti-CD2 antibody, anti-CD3 antibody and anti-CD28 antibody or magnetic bead labeled with these antibodies, or a combination thereof. As for a combination, the agents can be mixed in any proportion. In order to increase the proliferation rate of DNT cells, various cytokines such as IL-2 and/or IL-15 or the combination thereof can be added. The total DNT cells are collected after culturing and amplification. The IL-17 producing DNT cell subpopulation is removed by using an antibody targeting Lgals1, Ly6a, CXCR6, S100a6, Lgals3, Lta, ICOS or S100a10, or a combination of these antibodies. At the same time, negative sorting is performed by using magnetic beads labeled with antibodies against CD4, CD8 and NK1.1 (for mouse)/CD56 (for human) in order to remove the possible CD4, CD8 and NK cells from the culture and obtain cultured DNT cells for subsequent therapy. The phenotype of cultured and amplified DNT cells is CD3+TCRαβ±CD4−CD8−NK1.1− (for mouse)/CD56− (for human) CD19−TCRγδ±.

3. Method to culture and amplify antigen specific DNT cells is shown as follows.

PBMCs are obtained from mice or human spleen or peripheral blood under sterile condition. Mononuclear cell suspension is obtained via gradient centrifugal method. The mononuclear cells are labeled with antibodies against CD19, CD4, CD8, TCR-γδ, NK1.1 (for mouse)/CD56 (for human), aGalcer-CD1d and LPC-CD1d tetramer (or TCRVα24-Jα18 antibody) (in order to remove B cells, CD4 and CD8 T cells, γδ T cells, type 1 NKT cells and type 2 NKT cells, respectively) and then negative sorted (via sorting method such as magnetic bead sorting, fluorescence activated cell sorting, density gradient centrifugation, etc.), thereby obtaining a cell subpopulation dominated by DNT cells. At the same time, the IL-17 producing DNT cell subpopulation is removed by using an antibody targeting S100a6, CXCR6, ICOS, CCR2, CD82, CD127 or Ltb4r, or a combination of these antibodies. Then DNT cells were co-cultured in vitro with cells which are antigen-present cells, such as macrophages, dendritic cells and B-cells. At the same time, specific antigen peptides can be added to enhance the antigen specificity. Various cytokines such as IL-2 and/or IL-15 or the combination thereof can be added into culture. In order to enhance the in vitro amplification capability, CD3 antibody can be added at the same time. Cells are collected after culturing for 7-10 days, and are negative sorted by using magnetic beads labeled with antibodies against CD4, CD8 and NK1.1 (for mouse)/CD56 (for human) so as to remove possible CD4, CD8 and NK cells from the culture. At the same time, antigen-present cells such as B cells and dendritic cells in the co-culture system are removed by using magnetic beads labeled with antibodies against CD19, CD11b and/or CD11c. DNT cells are purified and obtained for subsequent therapy. The phenotype of cultured and amplified DNT cells is CD3+TCRαβ±CD4−CD8−NK1.1− (for mouse)/CD56− (for human) CD19-TCRγδ±.

Composition and Method of Administration

The present invention also provides a pharmaceutical composition in the fourth aspect of the invention, which contains the cell preparation according to the first aspect of the present invention, and, by inhibiting the proliferation of T cells and/or inducing the apoptosis of T cells, is useful for treatment of a disease selected from the group consisting of:

tumor, infection disease, metabolic syndrome (obesity, insulin resistance, type 2 diabetes, steatohepatitis and coronal atherosclerosis heart disease), stroke, and a combination thereof. The diseases further comprise allergic asthma, type 1 diabetes, lupus erythematosus, rheumatoid arthritis, Sjogren's Syndrome, psoriasis, multiple sclerosis, autoimmune hepatitis, primary biliary cirrhosis and sclerosing cholangitis, Hashimoto's thyroiditis, autoimmune kidney disease, organ transplantation rejection, graft-versus-host disease and a combination thereof.

The present invention also provides a pharmaceutical composition, which contains a safe and effective amount of the cell preparation of the present invention and a pharmaceutically acceptable carrier or excipient. Such carrier comprises (but is not limited to): saline, buffer, glucose, water, glycerin, ethanol, powder, dimethyl sulfoxide (DMSO) and combinations thereof. The pharmaceutical preparation should match the mode of administration. The pharmaceutical composition of the present invention can be prepared in the form of an injection, which is prepared, for example, by a conventional method using physiological saline or an aqueous solution containing glucose and other adjuvants. The administration amount of the active ingredient is a therapeutically effective amount. In addition, the cell preparation of the present invention can be administered in combination with other therapeutic agents.

As for the pharmaceutical composition of the present invention, it can be applied to a subject in need (e.g. human and non-human mammal) by using conventional methods. Representative methods of administration comprise (but are not limited to) injection into various parts: intravenous injection, intra-arterial injection, intrapleural, injection abdominal and pelvic injection, subarachnoid injection, sinus injection, intracerebral injection and injection into various tissues (e.g. tumor tissue and inflammatory tissue), etc.

Main Advantages of the Present Invention (a) The present invention provides a system for amplification and purification of DNT cells.

(B) IL-17 is an important inflammatory cytokine, and can induce autoimmune response and inflammatory response of body. The purified DNT cells of the present invention is unable to secrete IL-17, thereby avoiding the side affect of autoimmune response and inflammatory response of cell therapy receptors induced by IL-17.

(C) The purified DNT cells of the present invention have a stronger immunosuppressive function than that in unpurified DNT cells and useful for treatment of various autoimmune diseases, allergic asthma and inflammatory-related diseases.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions proposed by the manufacturer. Unless otherwise stated, the percentage and parts are calculated based on weight.

Example 1

Single-Cell Sequencing

Analysis of DNT cells from mice spleen was carried out at single-cell level by using single-cell transcriptome sequencing techniques. Firstly, TCRαβ+CD4-CD8-NK1.1-double negative T cells were obtained by using fluorescence-activated cell sorting technology (see FIG. 1). Type 1 NKT (positive for anti-aGalcer-CD1d tetramer antibody) and type 2 NKT (positive for anti-LPC-CD1d tetramer antibody) cells were further removed by using antibody against CD1d tetramer via staining technology. Then single-cell transcriptome sequencing and analyzing of the purified naïve DNT cells were carried out in order to detect whether the IL-17 producing DNT cell subpopulation existed.

Figure 2:
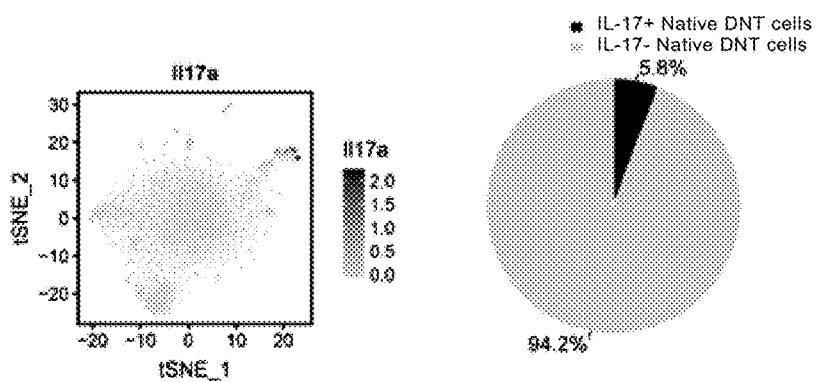
FIG. 2 shows the single-cell subpopulation analysis of naïve DNT cells (IL-17 producing subpopulation exists and accounts for about 5.8% of the total number of initial DNT cells).
Figure 3:
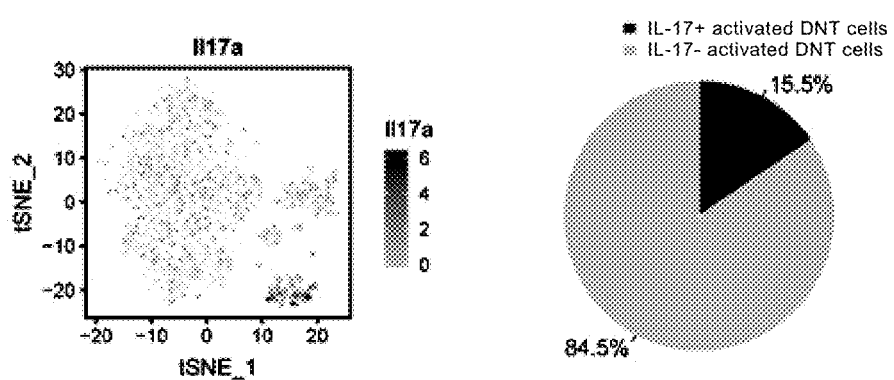
FIG. 3 shows the single-cell subpopulation analysis of purified DNT cells which have been in vitro stimulated for activation and proliferated (IL-17 producing subpopulation exists and accounts for 15.5% of the total number of proliferated cells).

The results of single-cell sequencing and PCR verification showed that in purified DNT cells, mRNA expression level in some cell subpopulation, which was about 5.8% of the total DNT cells, was higher than in that in other DNT cells (see FIG. 2). After the purified total DNT cells were stimulated in vitro with CD3/28 antibodies for 3 days, the proliferation of IL-17 producing DNT cell subpopulation was significantly amplified and the DNT cells highly expressing IL-17 mRNA could reach 15.5% of total DNT cells (see FIG. 3). It demonstrated that after in vitro stimulation for activation and proliferation, the proliferation of IL-17 producing DNT cell was significantly higher than that of other DNT cells. If these DNT cells are used for infusion therapy, they may cause receptor immune activation and even occurrence of autoimmune response.

Figure 4:
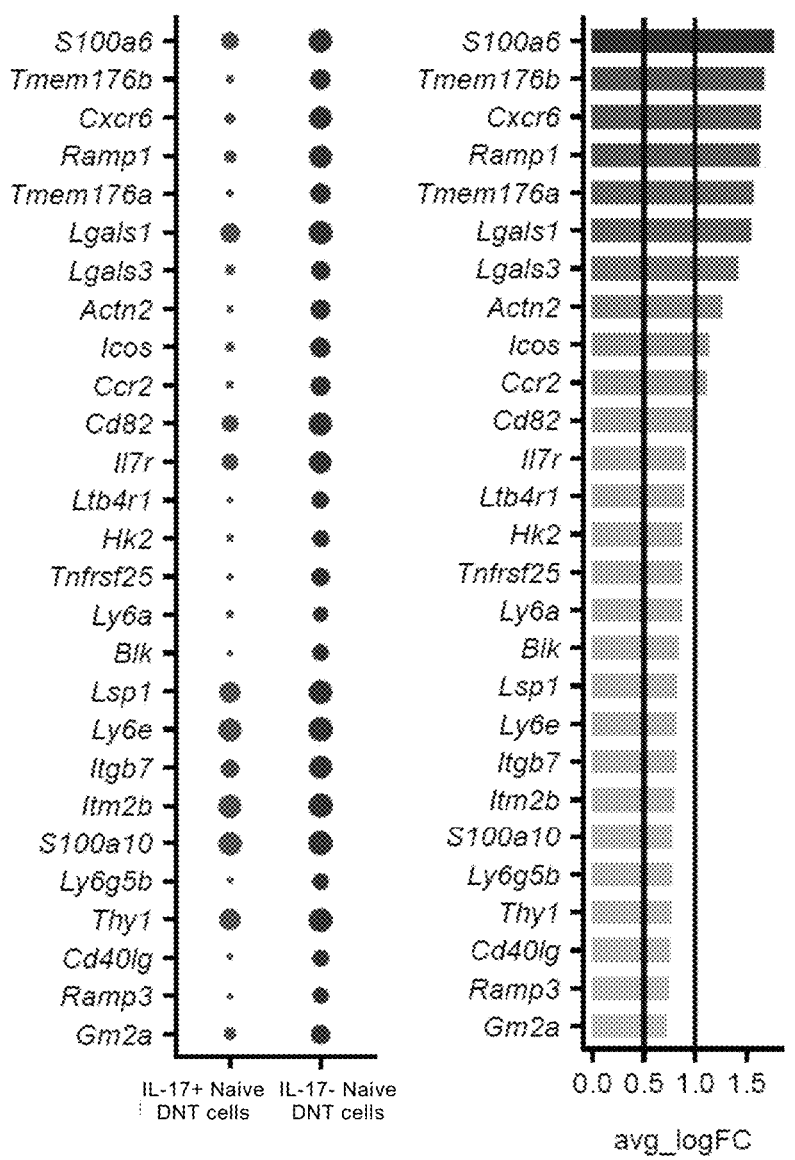
FIG. 4 shows the expression levels of cell membrane protein genes in IL-17 producing naïve DNT cell subpopulation.

Total Naïve DNT cells were further analyzed in order to remove such IL-17 producing DNT cells. Results showed that these IL-17 producing naïve DNT cells expressed ultra-high level of various transmembrane proteins, wherein the expression of S100a6, Tmem176b, CXCR6, Ramp1, Tmem176a, Lgals1, Lgals3, ACTN2, ICOS, CCR2, CD82, CD127 (IL7r), Ltb4r1, Hk2, TNFRSF25, Ly6a, BLK, Lsp1, Ly6e, Itgb7, Itm2b, S100a10, Ly6g5b, Thy1, CD40lg, Ramp3, Gm2a, etc. was increased by more than 0.5 fold as compared with other DNT cells, and, in particular, the expression of proteins such as S100a6, Tmem176b, CXCR6, Ramp1, Tmem176a, Lgals1, Lgals3, ACTN2, ICOS, CCR2, CD82, CD127(IL7r) was increased by more than 1 fold as compared with other DNT cells (See FIG. 4). Therefore, the antibodies targeting these differentially expressed proteins as mentioned above (including but not limited to S100a6, CXCR6, ICOS, CCR2, CD82, CD127, Ltb4r, etc.) are useful for purifying and separating the IL-17 producing naïve DNT cell subpopulation.

Figure 5:
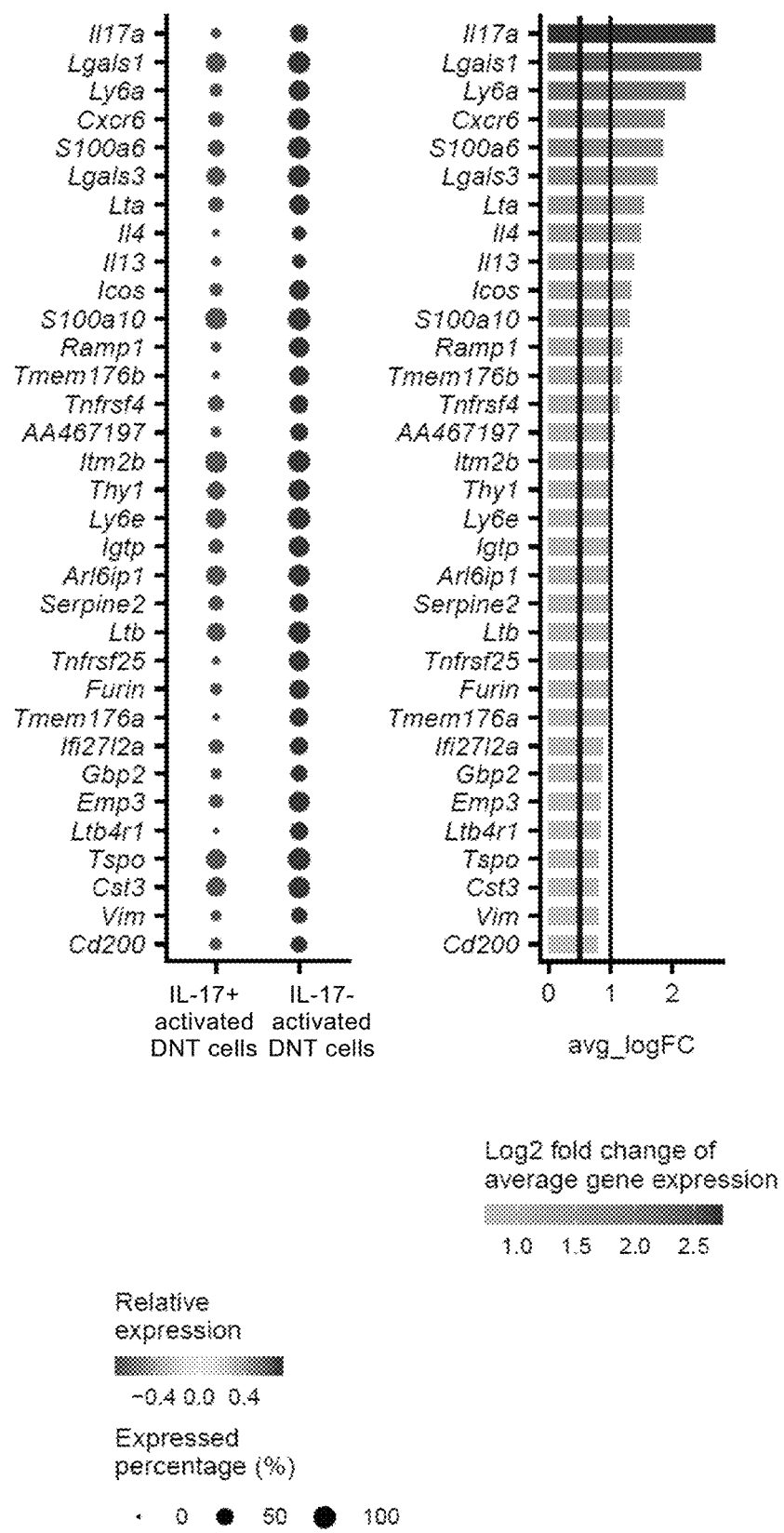
FIG. 5 shows the expression levels of cell membrane protein genes in activated IL-17 producing DNT cell subpopulation.

Then the naïve total DNT cells were stimulated using CD3/28 antibodies for 3 days, and the activated and proliferated DNT cells were analyzed using single-cell sequencing. The results were shown in FIG. 5. The activated IL-17 producing DNT cell subpopulation highly expressed secretory and transmembrane proteins, e.g. IL-17a, Lgals1, Ly6a, CXCR6, S100a6, Lgals3, Lta, IL-4, IL-3, ICOS, S100a10, Ramp1, Tmem176b, Tnfrsf4, AA467197, Itm2b, Thy1, Igtp, Arl6ip1, Serpine2, Ltb, Tnfrsf25, Furin, Tmem176a, Ifi27l2a, Gbp2, Emp3, Ltb4r1, Tspo, Cst3, Vim, CD200, etc. The antibodies targeting these proteins are useful for sorting the activated IL-17 producing DNT cell subpopulation.

Example 2

Purification of DNT Cells and Verification of Effectiveness Thereof

In order to further support the findings above, firstly, mouse naïve DNT cells were purified by obtaining the mouse spleen under sterile conditions, grinding it and lysing red blood cells to obtain the single-cell suspension of spleen cells. Spleen cells from mouse were labeled with antibodies against CD19, CD4, CD8, TCR-γδ, NK1.1, aGalcer-CD1d and LPC-CD1d tetramer (or TCRVα24-Jα18 antibody) and negative sorted using magnetic beads, thereby obtaining a cell subpopulation dominated by DNT cells. At the same time, the IL-17 producing DNT cell subpopulation was labeled with an antibody targeting any one of S100a6, CXCR6, ICOS, CCR2, CD82, CD127 and Ltb4r.

Then same amount of naïve total DNT cells, IL-17 producing DNT cells and the remaining DNT cells from which IL-17 producing DNT cells were removed, were stimulated for amplification in vitro by using CD3/CD28 antibodies, respectively.

Figure 6:
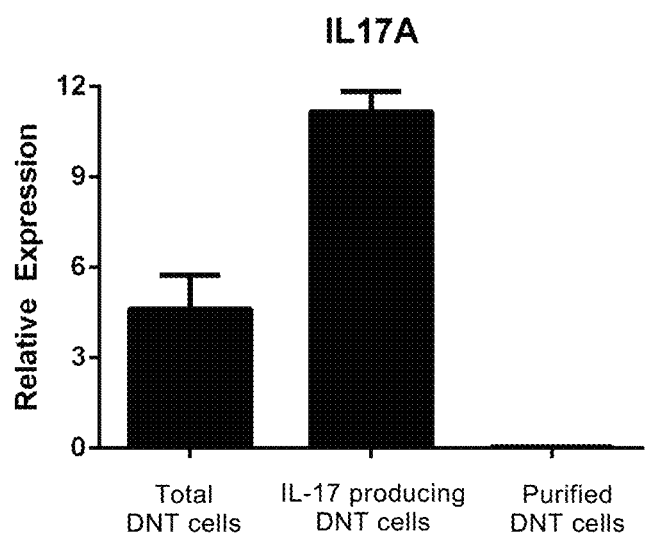
FIG. 6 shows the results of in vitro stimulation experiments for each groups of cells. Specifically, purified naïve total DNT cells, IL-17 producing DNT cells, and DNT cells from which IL-17 producing DNT cells were removed, were stimulated for amplification in vitro using CD3/CD28 antibodies, respectively. PCR verification was performed after 3 days and it was found that in total DNT cell group, after activated and proliferated, there was IL-17 expression; the IL-17 producing DNT cells after proliferation had a significantly higher IL-17 expression than that in the total DNT cell group; and in the DNT cells from which IL-17 producing DNT cells were previously removed (purified DNT), no IL-17 secretion or expression was detected after activation and proliferation.

The results were shown in FIG. 6. After stimulated for 3 days, total DNT cell group expressed IL-17; after amplification, the IL-17 producing DNT cells had a higher expression of IL-17 than that in the total DNT cell group; and after stimulated by CD3/28 in vitro, there was no IL-17 secretion or expression in the activated and proliferated DNT cells from which IL-17 producing DNT cells were previously removed so that it proved the effectiveness of pre-removal treatment. The results above have shown that pre-removing S100a6, CXCR6, ICOS, CCR2, CD82, CD127 or Ltb4r positive DNT cells can efficiently remove the IL-17 producing DNT cell subpopulation and avoid further amplification thereof.

Figure 7:
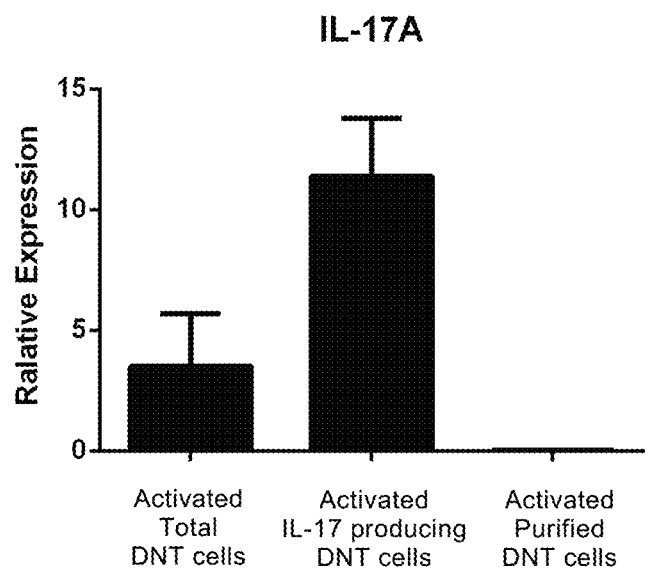
FIG. 7 shows the results of the in vitro stimulation experiments for each group of cells. Specifically, total naïve DNT cells were stimulated for 3 days using CD3/28 antibodies and were sorted and purified via flow cytometry by using markers on the cell surface of IL-17 producing DNT cell subpopulation. It was found in the study that the IL-17 producing DNT cell subpopulation significantly expressed IL-17 while the rest DNT cells, from which the activated IL-17 producing DNT cell subpopulation was removed, did not express the inflammatory cytokine IL-17.

Further, the total naïve DNT cells were stimulated with CD3/28 antibodies for 3 days and the cells are separated and purified by using antibodies targeting Lgals1, Ly6a, CXCR6, S100a6, Lgals3, Lta, ICOS, S100a10 or Tnfrsf4, etc. It was found by PCR verification that this subpopulation of activated DNT which were separated and purified with those antibodies significantly expressed IL-17, while the rest DNT cells, from which the activated IL-17 producing DNT cell subpopulation was removed, did not express the inflammatory cytokine of IL-17 (see FIG. 7).

Comparison of these two methods, i.e., method of purifying DNT cells before culture amplification and method of purifying DNT cells after culture amplification, has shown that the former uses significantly less antibody than the latter. In the following verification of function, the first method was used, i.e. the method of pre-removing IL-17 producing DNT cells before culture amplification of DNT cells.

Example 3

Verification of Function of Purified DNT Cells

In order to verify the in vitro immunosuppressive function of purified DNT cells, the purified and proliferated DNT cells were cultured together with T lymphocytes from the same kind of mice which were stimulated by dendritic cells for proliferation.

Figure 8:
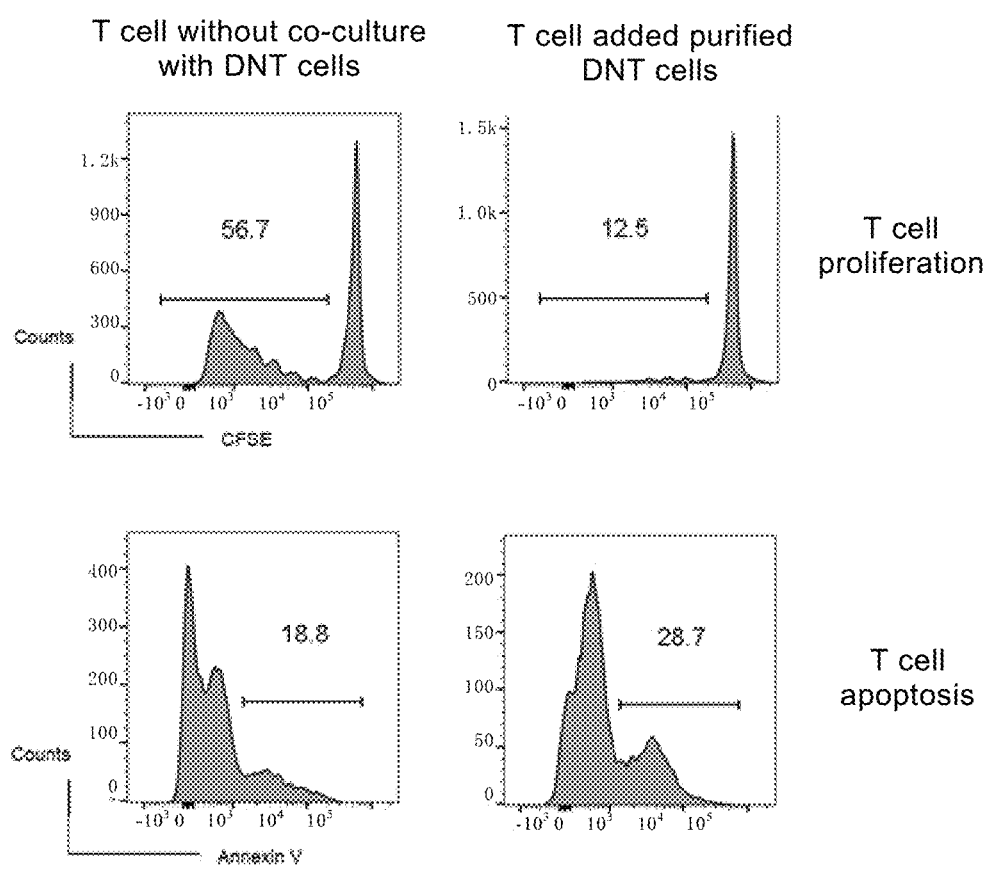
FIG. 8 shows that DNT cells obtained based on the optimized in vitro amplification culture system of mouse DNT cells could significantly inhibit T cell proliferation and induce T cell apoptosis.

The results was shown in FIG. 8. The purified DNT cells had significant effects of inhibiting T cell proliferation and inducing apoptosis.

Then the models of obesity, diabetes and steatohepatitis mice were established by induction with using high-fat diets, and the inhibitory effect of DNT cells on inflammatory in vivo was studied. After high-fat diet for 8 weeks, the mice were administered a single injection of $3\text{-}5\times10^6$ DNT cells followed by high-fat diet for another 8 weeks (totally 16 weeks).

Figure 9:
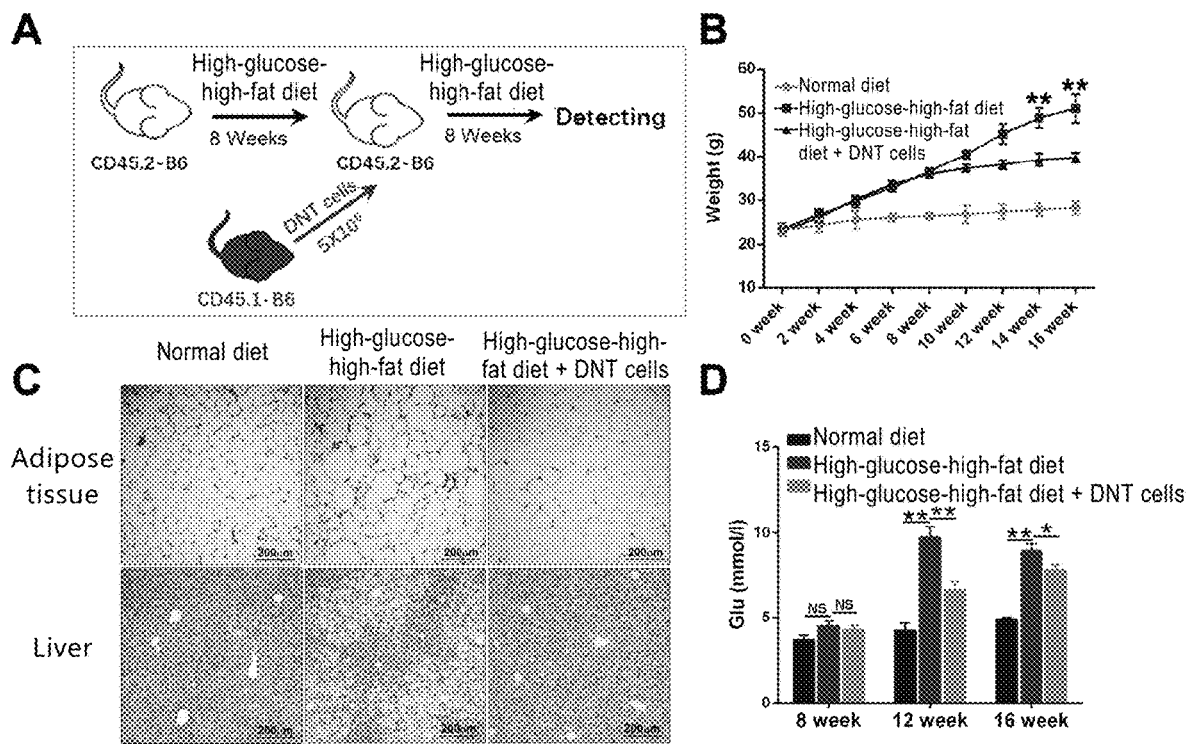
FIG. 9 shows that DNT cells obtained based on the optimized in vitro amplification culture system of mouse DNT cells had significant in vivo immunosuppressive function and had good preventative and therapeutic effects on obesity, insulin resistance and steatohepatitis induced by diet. Among them.

The results were shown in FIG. 9. The condition of weight, fasting blood sugar and fatty liver of mice in DNT cell treatment group were all improved, and related to DNT cells which inhibited inflammation of adipose tissue and improved insulin resistance.

Figure 10:
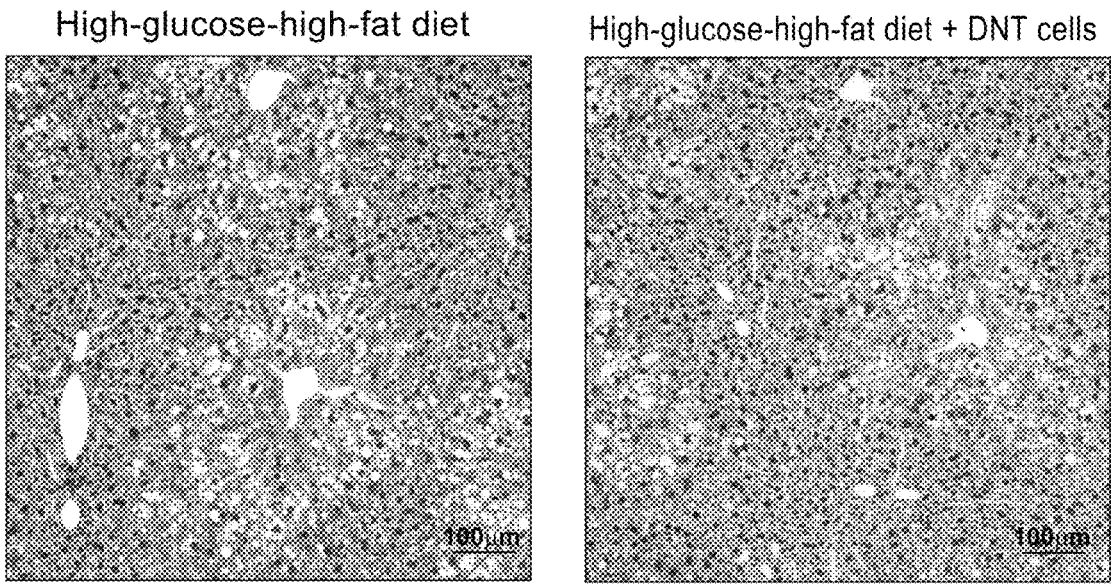
FIG. 10 shows that the liver fat follicle degeneration and inflammatory cell accumulation of mice in the total DNT cells (from which IL-17 producing DNT cells were not previously removed) infusion treated group were not significantly improved as compared with the control group, and phenomenon of fat follicle and inflammatory cell infiltration still existed.

However, if the total DNT cells were injected (from which IL-17 producing DNT cells were not previously removed), the liver fat follicle degeneration and inflammatory cell accumulation of mice in the treated group were not significantly improved as compared with the control group, and phenomenon of fat follicle and inflammatory cell infiltration still existed (FIG. 10).

Example 4

Culture of Antigen Specific DNT Cells

In order to study the antigen specific immunosuppression of DNT cells, a mouse allergic asthma model induced by OVA was firstly established. Then the purified naïve DNT cells were in vitro cultured together with mature mice dendritic cells. OVA-specific OVA323-339 antigen peptides or OVA-nonspecific MOG33-55 antigen peptides were added into the culture. The antigen specific inhibitory effect of DNT cells after stimulation and proliferation was observed.

Figure 11:
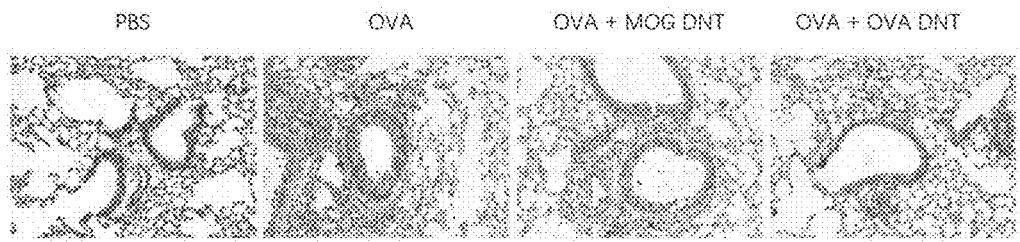
FIG. 11 shows that DNT cells stimulated and proliferated by OVA323-339 polypeptides have significant protective effects on allergic asthma stimulated by OVA antigens and can significantly alleviate allergic airway inflammation and accumulation of pulmonary eosinophils and lymphocytes, while DNT cells induced by unrelated OVA peptide (MOG33-55) have no protective effect on mouse asthma induced by OVA.

The results were shown in FIG. 11. For allergic asthma stimulated by OVA protein, after twice OVA sensitization, infusion of DNT cells proliferated and stimulated by OVA323-339 polypeptide had a good inhibitory effect on asthma attack.

Meanwhile, DNT cells stimulated in vitro by unrelated MOG33-55 peptide had no good preventive or therapeutic effects on asthma induced by OVA protein. It proved that DNT cultured and amplified in vitro had significant antigen-specific immunosuppressive effect.

Figure 12:
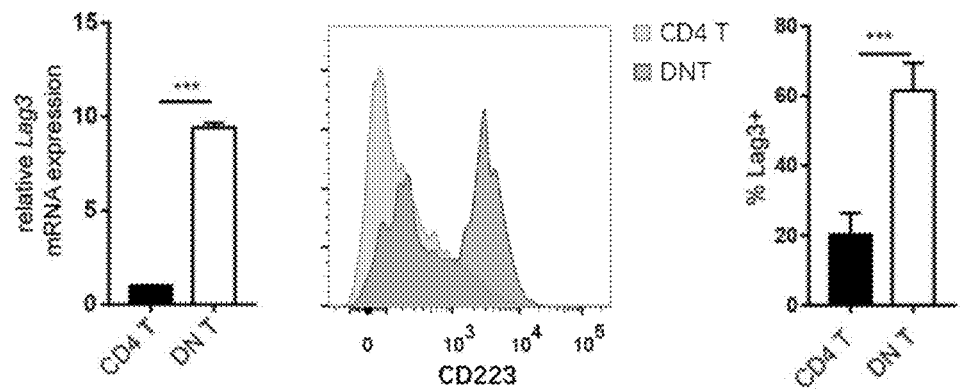
FIG. 12 shows that compared with CD4 T cells, DNT cells express a higher level of LAG3 molecule.

Compared with CD4 T cells, it was found that DNT cells expressed a higher level of LAG3 molecule (see FIG. 12). Lag3 molecule could combine with MHC-II molecule and the affinity to MHC-II molecule thereof was much stronger than that of CD4 molecule.

Figure 13:
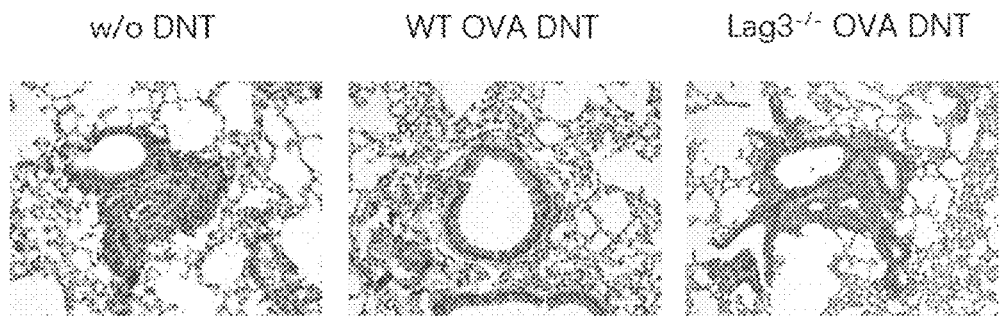
FIG. 13 shows that compared with wild type DNT cells, LAG3 knocked-out DNT cells have a significantly decreasing preventative and therapeutic effects on asthma induced by OVA.
Figure 14:
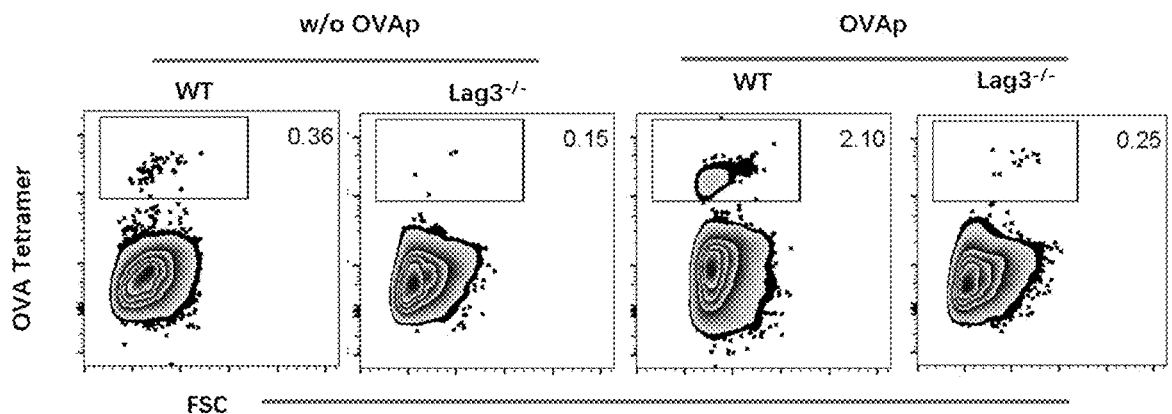
FIG. 14 shows that I-Ab OVA323-339 tetramer positive cells had significantly higher appearance frequency in DNT cells stimulated by OVA than that in Lag3 knocked-out DNT cells stimulated by OVA or in wild type DNT cells without OVA stimulation.

The wild type DNT cells and LAG3 knocked-out DNT cells were stimulated in vitro by OVA323-339 peptides respectively. Then the preventive and therapeutic effects for both cells on OVA-induced allergic asthma were observed. The results was shown in FIG. 13 and FIG. 14. The immune protective effect of LAG3 knocked-out DNT cells decreased significantly. By straining with OVA specific MHC-II molecule (I-A$^b$ OVA$_{323\text{-}339}$ tetramers), it was found that the capability of recognizing I-A$^b$ OVA$_{323\text{-}339}$ tetramers in LAG3 knocked-out DNT cells decreased significantly, and caused the decrease of antigen specific immunosuppressive capability of DNT cells. Therefore, it has been proved that LAG3 molecule plays an important role in maintaining the antigen specificity of DNT cells.

Figure 15:
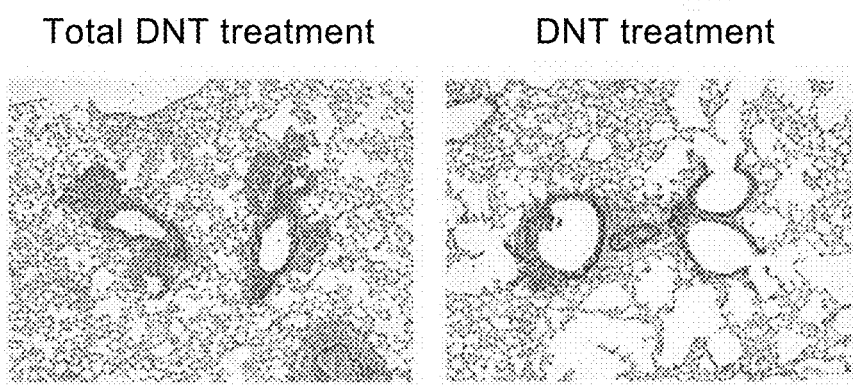
FIG. 15 shows that injection of DNT cells (purified DNT cells from which IL-17 producing DNT cells were removed) could completely relieve pulmonary lymphocyte infiltration. However, if the same amount of total DNT cells, from which IL-17 producing DNT cells were not previously removed, were injected, there was still significant lymphocyte infiltration around the alveoli, and the asthma could not be completely relieved.

However, if the same amount of total DNT cells (from which IL-17 producing DNT cells were not previously removed) were injected, there was still significant lymphocyte infiltration around the alveoli, and the asthma could not be completely relieved (FIG. 15).

Example 5

Verification of Function of Human DNT Cells

In order to further verify the in vitro immunosuppressive function of purified human DNT cells, human DNT cells were purified and amplified by using the method according to Example 2, and were cultured together with T lymphocytes proliferated and stimulated by dendritic cells (DC).

Figure 16:
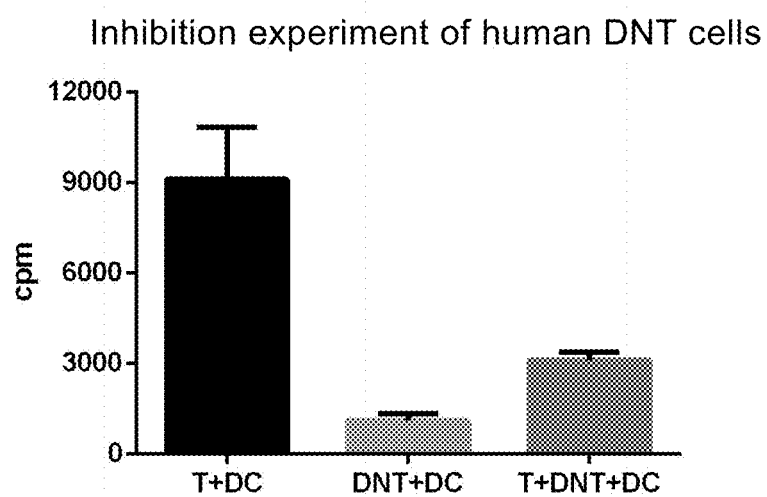
FIG. 16 shows that DNT cells obtained based on the optimized in vitro amplification culture system of human DNT cells have significant inhibitory effect on T cell proliferation.

The results were shown in FIG. 16. The purified DNT cells had significant inhibitory effect on T cell proliferation.

All literatures mentioned in the present application are incorporated by reference herein, as if each literature is individually incorporated by reference. Additionally, it should be understood that after reading the above teaching, many variations and modifications can made by the skilled in the art, and these equivalents also fall within the scope as defined by the appended claims.

The invention claimed is:

1. A cell preparation comprising a CD4$^-$CD8$^-$ Double Negative T cell (DNT cell) population, wherein in the CD4⁻CD8⁻ DNT cell population more than 95% of the total number of cells do not secrete IL-17;
  wherein the cell preparation is prepared through a method comprising the steps of:
  (a) providing a peripheral blood mononuclear cell population (PBMC cell population), and sorting the PBMC cell population, thereby obtaining a first cell subpopulation dominated by CD4⁻ CD8⁻ DNT cells;
  (b) removing IL-17 secreting DNT cells from the first cell subpopulation, expanding the remained first cell subpopulation, thereby obtaining a second cell subpopulation;
  (c) optionally, further removing IL-17 secreting DNT cells from the second cell subpopulation thereby obtaining a third cell subpopulation;
  (d) mixing the second or the third cell subpopulation with a carrier, thereby obtaining the cell preparation;
  wherein, in step (b), the IL-17 producing DNT cells are removed before expansion by using one or more antibodies targeting an expression protein selected from the group consisting of S100a6, CXCR6, ICOS, CCR2, CD82, CD127, Ltb4r and a combination thereof.

2. The cell preparation according to claim 1, wherein in the DNT cell population, more than 95% of the total number of cells have surface antigens CD3+ and TCR.

3. The cell preparation according to claim 1, wherein, in the DNT cell population, more than 50% of the total number of cells express the LAG3 gene.

4. A pharmaceutical composition comprising the cell preparation of claim 1, and a pharmaceutically acceptable carrier, diluent or excipient.

5. The cell preparation of claim 1, wherein in the DNT cell population, more than 98% of the total number of cells do not secrete IL-17.

6. The cell preparation of claim 1, wherein in the DNT cell population, more than 99% of the total number of cells do not secrete IL-17.

7. The cell preparation according to claim 1, wherein in the DNT cell population, more than 99.9% of the total number of cells do not secrete IL-17.

8. The cell preparation according to claim 1, wherein in step (b), the expansion culture is performed in the presence of a T cell stimulator selected from the group consisting of: CD3 antibody or magnetic bead labeled with CD3 antibody, CD28 antibody or magnetic bead labeled with CD28 antibody, and a combination thereof.

9. A method for preparing the cell preparation of claim 1, comprises:
  (a) providing a peripheral blood mononuclear cell population (PBMC cell population), and sorting the PBMC cell population, thereby obtaining a first cell subpopulation dominated by CD4⁻CD8⁻ DNT cells;
  (b) removing IL-17 secreting DNT cells from the first cell subpopulation, expanding the remained first cell subpopulation, thereby obtaining a second cell subpopulation;
  (c) optionally, further removing IL-17 secreting DNT cells from the second cell subpopulation thereby obtaining a third cell subpopulation;
  (d) mixing the second or the third cell subpopulation with a carrier, thereby obtaining the cell preparation of claim 1;
  wherein, in step (b), the IL-17 producing DNT cells are removed before expansion by using one or more antibodies targeting an expression protein selected from the group consisting of S100a6, CXCR6, ICOS, CCR2, CD82, CD127, Ltb4r and a combination thereof.

10. The method according to claim 9, wherein in step (a), sorting the PBMC cell population comprises removing B cells, CD4 T cells, CD8 T cells, γδ T cells, type 1 Natural Killer T cells (NKT) and type 2 NKT cells, thereby obtaining the first cell subpopulation dominated by DNT cells.

11. The method according to claim 9, wherein in step (b), expanding comprises use of antigen presenting cells and/or antigen peptides.

12. The method according to claim 9, wherein the PBMC cell population is from either mouse spleen or human peripheral blood.

13. The method according to claim 9, wherein in step (b), the expansion culture is performed in the presence of a T cell stimulator selected from the group consisting of: CD3 antibody or magnetic bead labeled with CD3 antibody, CD28 antibody or magnetic bead labeled with CD28 antibody, and a combination thereof.

\* \* \* \* \*